United States Patent [19]

Cullen et al.

[11] Patent Number: 5,064,855
[45] Date of Patent: Nov. 12, 1991

[54] ACID POLYCYCLIC ETHER ANTIBIOTIC

[75] Inventors: Walter P. Cullen; James R. Hauske; Gloria J. Kostek; Hiroshi Maeda; Junsuke Tone, all of Groton, Conn.

[73] Assignee: Pfizer Inc., New York, N.Y.

[21] Appl. No.: 649,120

[22] Filed: Jan. 28, 1991

Related U.S. Application Data

[60] Continuation of Ser. No. 467,589, Jan. 19, 1990, abandoned, which is a division of Ser. No. 315,953, Feb. 27, 1989, Pat. No. 4,920,050.

[51] Int. Cl.$^5$ .................... A61K 31/35; C07D 311/00
[52] U.S. Cl. ..................... 514/460; 549/343
[58] Field of Search ................. 549/343; 514/460

[56] References Cited

U.S. PATENT DOCUMENTS

| | | | |
|---|---|---|---|
| 3,501,568 | 3/1970 | Haney et al. | 514/460 |
| 3,947,586 | 3/1976 | Messersmith | 514/460 |
| 4,293,650 | 10/1981 | Florent et al. | 435/886 |
| 4,294,925 | 10/1981 | Liu et al. | 435/886 |
| 4,309,509 | 1/1982 | Kostner et al. | 435/886 |
| 4,329,426 | 5/1982 | Deushi et al. | 435/886 |
| 4,366,168 | 12/1982 | Clinton et al. | 514/449 |
| 4,468,380 | 8/1984 | O'Doherty et al. | 514/460 |
| 4,495,286 | 1/1985 | Tunac et al. | 435/886 |
| 4,503,152 | 3/1985 | Omura et al. | 435/118 |
| 4,540,661 | 9/1985 | Hannon et al. | 435/128 |
| 4,547,523 | 10/1985 | Celmer et al. | 435/886 |

OTHER PUBLICATIONS

Occolowitz et al. in Westley, ed., "Polyether Antibiotics, Naturally Occurring Acid Ionophores," vol. 2, Marcel Dekker, Inc., New York and Basel, 1982, pp. 197, 219–223.

Merck Index, Tenth Edition, Merck & Co., Inc., Rahway, N.J., 1983, monograph 6100 at p. 893.

*Primary Examiner*—C. Warren Ivy
*Assistant Examiner*—A. A. Owens
*Attorney, Agent, or Firm*—Peter C. Richardson; J. Trevor Lumb; Mervin E. Brokke

[57] ABSTRACT

An acidic polycyclic ether antibiotic, having structure established by X-ray crystallography, is formed by fermentation of a novel microorganism, Streptomyces sp. ATCC 53862. This novel antibiotic is useful as an anticoccidial in chickens, in the prevention or treatment of swine dysentery, and as a growth promotant in cattle and swine.

9 Claims, No Drawings

ACID POLYCYCLIC ETHER ANTIBIOTIC

This is a continuation of application Ser. No. 07/467,589, filed on Jan. 19, 1990 now abandoned; which is a division of application Ser. No. 07/315,953, filed on Feb. 27, 1989, now U.S. Pat. No. 4,920,050.

BACKGROUND OF THE INVENTION

The present invention concerns a new acidic polycyclic ether antibiotic having the formula:

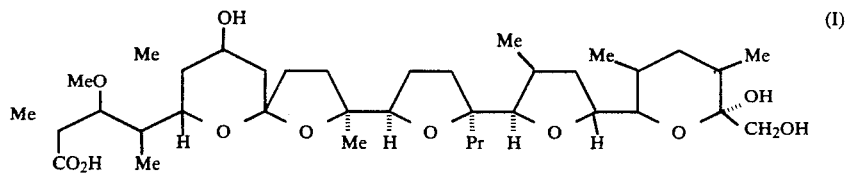

wherein Me=CH$_3$ and Pr=CH$_3$CH$_2$CH$_2$, having absolute stereochemistry as shown; pharmaceutically acceptable cationic salts thereof; nutrient feed compositions comprising said antibiotic for poultry, cattle or swine; its use as an anticoccidial agent in poultry, in the treatment or prevention of swine dysentery, or as a growth promotant in cattle or swine; a fermentation method for its preparation; and the Streptomyces sp. microorganism which produces said antibiotic in said fermentation method.

The compound (I), which is a homolog of monensin, is a new member of the acidic polycyclic ether group of antibiotics. This family includes, in addition to monensin (The Merck Index, 10th Ed., Merck and Co., Inc., Rahway, N.J., 1983, monograph no. 6100), such well known agents as nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 177-223 (1977). These compounds are generally known as coccidiostats, as feed additive-growth promotants, and/or as agents useful against swine dysentery.

SUMMARY OF THE INVENTION

A culture of Streptomyces sp., ATCC 53862, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Streptomyces sp. ATCC 53862 in an aqueous nutrient medium comprising an assimilable source of carbon and nitrogen until a recoverable amount of said compound of the formula (I) is formed, preferably under submerged aerobic conditions. For use as an anticoccidial agent, in the prevention or treatment of swine dysentery, and/or as a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylenediamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, or to prevent or treat dysentery in swine; and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; to a method for preventing or treating dysentery in swine which comprises administering to said swine a compound of the formula (I) in an amount effective in preventing or treating said dysentery in said swine; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of Streptomyces sp. ATCC 53862, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Streptomyces sp., and has been deposited under the Budapest Treaty in The American Type Culture Collection, Rockville, Md. as the type culture under their accession number ATCC 53862. This culture will be irrevocably and without restriction or condition released to the public upon issuance of a patent. Permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 122. All restrictions on the availability to the public of the culture deposited will be irrevocably removed upon granting of the patent.

This novel culture was derived from a soil sample collected in Arnprior, Ontario, Canada and identified in the culture collection of Pfizer Inc. as N765-21. Its description and classification were provided by Dr. L. H. Huang. This culture was found to have the narrow hyphae of the Actinomycetales, an aerial mycelium which produces spore chains, and an unfragmented substrate mycelium. The results of the whole cell analyses further indicate that it belongs to the genus Streptomyces.

A slant culture of the microorganism was planted into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the results read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421-423 (1964), and Lechevalier, J. Lab. Clin. Med., Vol. 71, pp. 934-944 (1968), respectively. *Streptomyces flocculus* ATCC 25453 was used for purposes of comparison.

The culture was identified as follows:

Yeast Extract-Malt Extract Agar (ISP #2 medium, Difco)—Growth good, yellowish to yellowish brown (2 nc, 3 ic) with some white aerial mycelium; moderately raised, wrinkled; reverse yellowish (2 nc); soluble pigement yellowish brown (3 lc).

Oatmeal Agar (ISP #3 medium,—Growth moderate to good, cream (2 ca), with some white aerial mycelium; slightly raised, smooth; reverse cream to pale yellowish (2 ca, 2 ea); soluble pigment cream (2 ca).

Inorganic Salts-Starch Agar (ISP #4 medium, Difco)—Growth good, white to yellowish (2 ga, 2 ic); thin to raised, smooth to slightly wrinkled, with white aerial mycelium; reverse yellowish (2 ga, 2 ic); soluble pigment cream (2 ca).

Glycerol-Asparagine Agar (ISP #5 medium, Difco)—Growth poor to moderate, cream (2 ca), thin, smooth, or appearing as isolated colonies; aerial mycelium sparse, white; reverse cream (2 ca); no soluble pigment.

Czapek-Sucrose Agar (Waksman, "The Actinomycetes", v. 2, medium #1, p. 328, 1961)—Growth moderate, cream to pale yellowish (2 ca, 2 ea); thin to slightly raised, smooth, with white aerial mycelium; reverse same as surface; no soluble pigment.

Glucose-Asparagine Agar (ibid., medium #2)—Growth moderate to good, cream to yellowish (2 ca, 2 ga); slightly to moderate raised, smooth to wrinkled; aerial mycelium none or sparse, white; reverse pale yellowish (2 ea); soluble pigment cream (2 ca).

Gordon and Smith's Tyrosine Agar (Gordon and Smith, J. Bacteriol., 69:147-150, 1955)—Growth moderate, cream (2 ca), thin to slightly raised, smooth, no aerial mycelium; reverse pale yellowish (2 ea); soluble pigment yellowish (2 ga).

Casein Agar (Gordon and Smith, ibid.)—Growth moderate to good, cream (2 ca), moderately raised, smooth to slightly wrinkled, no aerial mycelium; reverse pale yellowish (2 ea); with yellowish (2 ga) soluble pigment.

Bennett's Agar (Waksman, loc. cit., medium #30, p. 331)—Growth good, yellowish to dark yellowish (2 ic, 2 gc); slightly to moderate raised, smooth to wrinkled; aerial mycelium sparse, white; reverse yellowish (2 ga, 2 ic); soluble pigment yellowish (2 ic).

Emerson's Agar (ibid., medium #28, p. 331)—Growth good, cream, yellowish brown to brown (2 ca, 3 ic, 3 ie); moderately raised, wrinkled, no aerial mycelium; reverse yellowish (2 ga, 2 lc); soluble pigment yellowish brown (3 lc).

Nutrient Agar (ibid., medium #14, p. 330)—Growth moderate, cream (2 ca), thin, smooth, no aerial mycelium; reverse cream to pale yellowish (2 ca, 2 ea); no soluble pigment.

Gelatin Agar (Gordon and Mihm, J. Bacteriol. 73, 15-27, 1957)—Growth good, cream (2 ca), moderately raised, smooth but wrinkled toward edge, no aerial mycelium; reverse cream (2 ca); no soluble pigment.

Starch Agar (ibid.)—Growth good, cream to pale yellowish (2 ca, 2 ea), moderately raised, wrinkled, no aerial mycelium; reverse pale yellowish (2 ea); no soluble pigment.

Potato Carrot Agar (Lechevalier, Lab. Clin. Med., 71, 934-944, 1968, but use only 30 g. potatoes, 2.5 g. carrots and 20 g. agar)—Growth moderate, cream (2 ca) with some white aerial mycelium; thin, smooth to slightly granular; reverse colorless to cream (2 ca); no soluble pigment.

Tap Water Agar (2%)—Growth poor to moderate, cream (2 ca), thin to submerged, smooth; aerial mycelium none to sparse, white; reverse colorless to cream (2 ca); no soluble pigment.

Morphological Properties—The morphological observations were made on ISP Medium 9 (carbohydrate utilization medium) plus sucrose after 14 days of incubation; spore mass in White color-series; spore chains in Section Rectiflexibles or Section Spirales, curved, hooked, looped or in open coils of up to three turns, or arranged as an irregular mass at the tip; 10 to 30 spores per spore chain; sporophores monopodially branched; spores elliptical to cylindrical, $1.2-2.0(-2.2) \times 0.8-1.0(-1.1)$ microns; smooth, as revealed by scanning electron microscopy.

Biochemical Properties—Melanin not produced; hydrogen sulfide produced; gelatin liquefied; starch hydrolyzed; nitrate reduced to nitrite in dextrose nitrate but not in organic nitrate; poor growth and no decomposition on Jensen's cellulose broth; no growth and no decomposition on Levine and Schoenlein's cellulose broth; coagulation and clearing on milk; casein digestion positive; tyrosine digestion negative. Carbohydrate utilization: glucose, arabinose, fructose, mannitol, rhamnose, sucrose, xylose, inositol and raffinose all utilized.

| | Temperature Relations | | |
|---|---|---|---|
| 21° C. | 28° C. | 37° C. | 45° C. |
| Excellent Growth | Excellent Growth | Good Growth | No Growth |

Whole-Cell Analysis—The whole-cell hydrolysates contained LL-diaminopimelic acid, glucose and mannose.

The culture N765-21 is characterized by the white color of spores in mass, the negative melanin reaction, and the smooth spores which are curved, hooked, looped or in an open coil of up to three turns. The substrate mycelium was cream, pale yellowish to yellowish. Except for some tints of cream, yellowish or yellowish brown, there were no distinct soluble pigments produced. The culture utilized glucose, arabinose, fructose, inositol, mannitol, raffinose, rhamnose, sucrose and xylose. The whole-cell hydrolysates indicate the presence of LL-diaminopimelic acid and the absence of diagnostic sugars.

Compared with the previously described species of Streptomyces, the culture N765-21 is related to S. pseudogriseolus, S. sclerotialus and S. flocculus. It differs from S. pseudogriseolus in its utilization of sucrose and raffinose. It is different from S. sclerotialus in its failure to produce sclerotia and its opened rather than compact spore chains.

When the culture N765-21 and S. flocculus ATCC 25453 were compared side-by-side, both resemble each other morphologically, culturally and biochemically. However, the culture N765-21 differs from S. flocculus in the positive starch hydrolysis, the failure to reduce organic nitrate, the poor rather than good growth on Jensen's cellulose broth, the failure to peptonize milk, the failure to grow at 45° C., and the positive rather than doubtful utilization of rhamnose.

On most of the media used, the culture N765-21 produced no or poor aerial mycelia, whereas S. flocculus produced abundant aerial mycelia. The substrate mycelium of the culture N765-21 was yellowish on Emerson's agar, and pale yellowish on casein agar and tyrosine agar; but that of S. flocculus was dark brown on Emerson's agar, yellow-brown on casein agar, and brown on tyrosine agar. The soluble pigments produced by S. flocculus were darker on some media, e.g., dark brown on Emerson's agar and tyrosine agar, and yellow-brown on casein agar.

On the basis of the data presented above, the culture N765-21 is considered as a member of the genus Streptomyces and designated Streptomyces sp. It has been deposited at the American Type Culture Collection under the accession number ATCC 53862.

The antibiotic compound (I) of the present invention is readily produced by the present Streptomyces sp. by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Streptomyces sp. ATCC 53862. The resulting vegetative cells are in turn used to inoculate shake flasks or inoculum tanks, also containing suitable growth media. Alternatively, the inoculum tanks are inoculated from the shake flasks.

Following a suitable growth period (generally 120 to 144 hours in shake flasks and 168 to 196 hours in inoculum tanks), a fermenter, also containing suitable growth media, is inoculated under aseptic conditions with vegetative broth from the shake flasks or inoculum tanks. Upon completion of growth (generally about 120-196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, Acta. Pathologica et Microbiologia Scandinav, Supp. 217, Section B: 64–68 [1971]), and employs brain heart infusion (BHI) agar and an inocula replicating device. Overnight growth tubes are diluted 100 fold for use as the standard inoculum (20,000–100,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as well as activity against Treponema hyodysenteriae, (the causative agent of swine dysentery) as illustrated in Table (I).

TABLE I

| IN VITRO ANTIBACTERIAL ACTIVITY OF THE COMPOUND OF THE FORMULA (I) | | |
|---|---|---|
| Organism | Strain No. | MIC. mcg/ml |
| Clostridium perfringens | 10A009 | less than 0.39 |
| Actinomyces pyogenes | 14D002 | less than 0.39 |
| Treponema hyodysenteriae | 94A007 | less than 0.39 |

Efficacy data for the compound of the formula (I) and its salts against coccidial infections in chickens is obtained by the following method. Groups of 3-5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3-5 ten-day old chicks are fed a similar mash diet without compound (I) or its salts. They are also infected after 24 hours and serve as infected controls. Yet another group of 3-5 ten-day old chicks are fed the same mash diet without antibiotic and are not infected with coccidia. These serve as normal controls. The results of treatment are evaluated after five days in the case of E. acervulina, and six days for all other challenges.

The criteria used to measure anticoccidial activity consists of lesion scores of 0 to 4 for E. tenella after J. E. Lynch, "A New Method of the Primary Evaluation of Anticoccidial Activity", Am. J. Vet. Res., 22, 324-326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.*, 28, 30-36, 1970. Activity is measured by dividing the lesion score of each treated group by the lesion score of the infected control. In this test, the compound (I) and its cationic salts exhibit excellent activity against *Eimeria tenella, E. acervulina, E. brunetti* and *E. necatrix* infections in poultry when incorporated into the mash diet of chickens at levels of about 20 to 100 ppm. For example, against a sensitive *E. tenella*, the compound of the formula (I) showed 100% control of lesions at doses as low as 50 ppm.

The present compound of the formula (I) is also generally useful in combination with certain other known anticoccidial agents, such as nicarbazin, 4,4'-dinitrocarbanilide or a naphthalenamine, as defined by Hamill et al., U.S. Pat. 4,582,822, cited above.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude form such as wet or dry mycelium or dried whole broth. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above. to produce concentrated supplements which are suitable for direct feeding to poultry In such instances, the poultry are permitted to consume the usual diet. Alternatively, such concentrated supplements are added directly to the poultry feed to product a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 20 to 100 ppm, preferably in the range of about 30 to 60 ppm. When administered in drinking water, the level which will be that which will provide the same daily dose of medication factored by the weight ratio of the average daily consumption of feed to the average daily consumption of water.

The activity of the compound of the formula (I) and its salts in promotion growth and/or increasing the efficiency of food utilization in swine or cattle can be measured directly by feeding test groups of animals various levels of the compound (I) or a salt in feed. Alternatively, British Patent Specification No. 1,197,826 details an in vitro rumen method for the evaluation of antibiotics in feeds.

For use in the prevention or treatment of swine dysentery, or in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of about 20 to 100 ppm. In ruminants the compound of the formula (I) can also be orally administered in the form of a bolus which is retained in the rumenoreticular sac, releasing the therapeutic agent at a substantially constant rate over a prolonged period of time, e.g., 4-8 weeks, providing a dose equivalent to that of the above daily dose in feed, i.e.:

$$\frac{\text{average daily dose}}{\text{in milligrams}} = \frac{(20 \text{ to } 100)}{\text{ppm}} \times \frac{\text{average daily feed}}{\text{consumption in Kg}}.$$

Exemplary of such a controlled release bolus is that of Cardinal, U.S. Pat. No. 4,601,893.

The present invention is illustrated by the following examples. However, it should be understood that the invention is not limited to the specific details of these examples.

EXAMPLE 1

Fermentation of Streptomyces sp. ATCC 53862
Isolation of the Compound (I) as the Sodium Salt The Streptomyces sp. was initially grown by inoculating solid media on slants or Roux bottles with the ATCC 53862 culture, using ATCC medium No. 172, prepared and having composition as follows.

|  | Grams/liter |
|---|---|
| Glucose | 10 |
| Soluble Starch | 20 |
| Yeast Extract | 5 |
| Casein Enzymatic Hydrolysate | 5 |
| Calcium Carbonate | 1 |
| Distilled Water to 1000 ml; pH to 7.0 with KOH; Add Agar | 20 |

Meanwhile, shake flasks were prepared using one or the other of the following media:

| C' | Grams/liter | JDYTT | Grams/liter |
|---|---|---|---|
| Cerelose | 10 | Cerelose | 10 |
| Soy Flour | 10 | Corn Starch | 5 |
| Corn Fermentation Solids | 5 | Corn Steep Liquor | 5 |
| Corn Starch | 10 | Casein Enzymatic Hydrolysate | 5 |
| Sodium Chloride | 5 | Cobalt Chloride | 0.002 |
| Cobalt Chloride | 0.002 | Calcium Carbonate | 3 |
| Calcium Carbonate | 1 | | |

One hundred ml of medium was distributed into 300 ml shake flasks and sterilized at 120° C. and 15 p.s.i. for 30 minutes. After cooling, the medium was inoculated with a vegetative cell suspension scraped from the above Streptomyces sp. slant culture. The flasks were shaken at 28° C. on a shaker having a displacement of 1.5 to 2.5 inches and 150 to 200 cycles per minute (CPM) for five to seven days.

Meanwhile, 5 liter fermentation vessels were prepared containing 3 liters of one of the above C' or JDYTT media or the following media:

| UK1-2 | Grams/liter |
|---|---|
| Cerelose | 45 |
| Soy Flour | 10 |
| Corn Steep Liquor | 10 |
| Cobalt Chloride | 0.002 |
| Magnesium Sulfate | 0.10 |
| Calcium Carbonate | 3 |
| Manganese Sulfate | 0.10 |
| Ferric Sulfate | 0.10 |

An antifoaming agent (polypropylene glycol, P2000, containing 10% ethylene oxide by weight, 1 ml) was added, and the vessels were sealed and sterilized at 120° C. and 15 p.s.i. for 45 minutes. The cooled vessels were then inoculated with one shake flask (ca 3%inoculum), fermented for 120 to 168 hours at 30° C., stirring at 1,700 revolutions per minute (RPM) with an air rate of one volume of air per volume of liquid per minute.

When the fermentation was completed (based on an antibiotic disc assay versus B. subtilis ATCC 6633) the fermenters were stopped and filtered at the natural pH with the aid of a diatomaceous earth. The filter cake was slurried in methanol, concentrated in vacuo, diluted with 2-3 volumes of water then extracted 2X with ½ to ½ volume of either methylisobutyl ketone or n-butanol. The solvent layer was separated from the aqueous phase by aspiration or centrifugation, sparkled and concentrated in vacuo to yield the antibiotic of the formula (I) in crude form as a viscous oil.

The bioactivity of the broth and subsequent recovery streams was followed by using a sensitive strain of Bacillus subtilis ATCC 6633 or Staphylococcus aureus ATCC 6538. The components in the broth and recovery streams can be visualized by using Analtech silica gel GF plates employing ethyl acetate as eluant. The developed plates were sprayed with vanillin reagent (3 g vanillin in 75 ml ethanol and 25 ml 85% phosphoric acid) and heated to 80° C. The antibiotic product of the formula (I) appears as an orange-brown spot. The developed tlc plate can also be overlayed with agar seeded with either S. aureus or B. subtilis to which 2,3,5-triphenyl-2H-tetrazolium chloride monohydrate has been added and incubated at 37° C. for 16 hours to visualize the antibiotic (white spots against a pink background).

In a second fermentation, sixty jar fermenters containing approximately 180 liters of fermented broth were recovered by extraction with ½ volume of methylisobutyl ketone, separated by extraction and concentration of the solvent, yield 31.6 g. The solid was chromatographed on silica gel gradiently eluted with chloroform followed by 0.5%, 1% and finally 2% $CH_3OH$ in $CHCl_3$. The activity was followed by tlc using silica gel plates developed with ethyl acetate and visualizing the active cuts with vanillin reagent at 80° C. The ionophore appears as orange brown bonds. Concentration of the active cuts produced 6.9 g of an oil, which was crystallized from warm diethyl ether to yield 2.62 g of crystalline compound (I). Reworking of the mother liquors yielded an additional 0.55 g of the same product.

EXAMPLE 2

Scale-up Fermentation

Scale-up in large fermentation vessels was carried out by preparing shake flasks containing 0.7 liters of C' or JDYTT medium. The shake flask inoculum was fermented for 5 to 7 days at 28° C., and used to inoculate a 6000 liter fermentation vessel containing 4,000 liters of JDYTT medium. Approximately one liter of inoculum was used in the tank. The fermentation, after proceeding for 7 to 10 days, was harvested.

The whole broth was extracted with 1,600 liters of methylisobutyl ketone at natural pH, and the layers separated on a DeLaval separator. The organic extract was concentrated under vacuum, first by vacuum pan and then on a cyclone still and rotary evaporator to yield 8 liters of an oil. This oil was chromatographed on column grade silica gel slurried in hexane. The column was developed with ethyl acetate. Product containing cuts, identified by tlc using the method described above, were combined, stripped and the residue taken up in ethyl acetate, treated with activated carbon, and filtered. The filtrate was shaken with dilute $H_3PO_4$ and then with dibasic sodium phosphate buffer to form the sodium salt, dried over $Na_2SO_4$, concentrated, and 24.4 g of the compound of the formula (I) crystallized as the sodium salt by the addition of heptane; tlc Rf 0.4 (10:1 $CHCl_3:CH_3OH$), 0.35 (ethyl acetate).

C-13 nmr [chemical shift (ppm) in $CDCl_3$ with number of hydrogens in parentheses]: 181.2* (0), 110.0 (0), 106.9 (0), 98.3* (0), 85.8* (1), 85.3 (0), 85.2 (1), 83.0* (1), 82.6 (1), 76.4* (1), 74.4 (1), 70.6 (1), 68.3* (1), 64.9* (2), 57.9 (3), 56.9 (3), 45.0* (1), 40.6 (2), 39.2* (2), 37.4 (1), 36.5* (1), 35.6 (2), 34.8* (1), 34.4 (1), 33.5* (2), 33.2* (2), 31.8* (1), 30.0 (2), 27.4* (3), 27.2 (2), 17.0 (2), 16.8* (3), 16.0* (3), 14.7 (3), 14.5* (3), 11.0* (3), and 10.5* (3).

*Monensin shows identical chemical shifts, and in addition peaks at 107.0 (0), 85.2 (0), 84.9 (1), 82.5 (1), 74.5 (1), 70.4 (1), 57.8 (3), 37.5 (1), 35.7 (2), 34.3 (1), 29.8 (2), 27.3 (2) and 8.1 (3).

The structure of the compound of the formula (I) was proven by X-ray crystallographic analysis.

We claim:

1. A compound having the formula

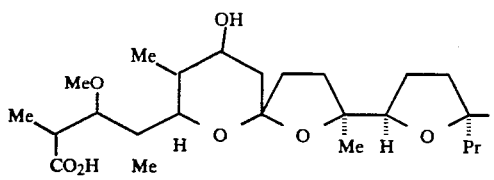

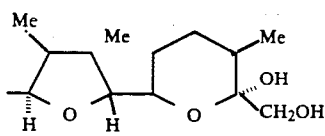

wherein Me=CH₃ and Pr=CH₃CH₂CH₂, or a pharmaceutically acceptable cationic salt thereof.

2. The compound of claim 1 in the form of its sodium salt.

3. A nutrient feed composition for cattle or swine which comprises the compound of claim 1 in an amount effective in preventing or treating dysentery in said swine, or in promoting growth of said cattle or swine.

4. A nutrient feed composition for poultry which comprises a compound of claim 1 in an amount effective to control coccidial infections in said poultry.

5. A method for promoting growth in swine or cattle which comprises administering to said swine or cattle a growth promoting amount of the compound of claim 1 in the form of a nutrient feed composition.

6. A method for preventing or treating dysentery in swine which comprises administering to said swine a compound of claim 1 in an amount effective in preventing or treating said dysentery in said swine.

7. A method of claim 6 wherein the compound is administered in the form of a nutrient feed composition.

8. A method for controlling coccidial infections in poultry which comprises administering to said poultry an anticoccidially effective amount of the compound of claim 1.

9. A method of claim 8 wherein the compound is administered to said poultry in the form of a nutrient feed composition.

* * * * *

UNITED STATES PATENT AND TRADEMARK OFFICE
CERTIFICATE OF CORRECTION

PATENT NO.    : 5,064,855
DATED         : November 12, 1991
INVENTOR(S)   : Walter P. Cullen et al.

It is certified that error appears in the above-identified patent and that said Letters Patent is hereby corrected as shown below:

Replace formula I, column 1, lines 12-19 with:

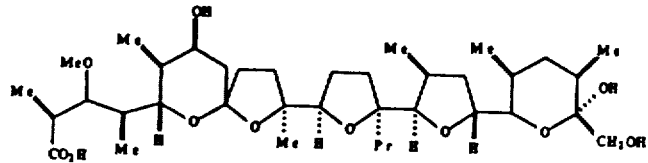

Replace the formula in claim 1, column 11 with:

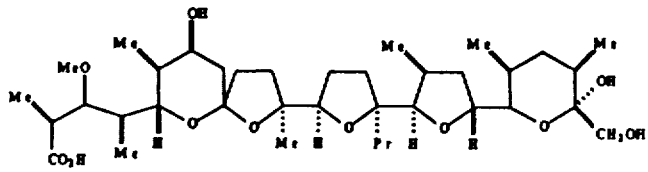

Signed and Sealed this

Twenty-seventh Day of April, 1993

*Attest:*

MICHAEL K. KIRK

*Attesting Officer*            Acting Commissioner of Patents and Trademarks